US00RE39498E

(19) United States
(12) Reissued Patent
Cham et al.

(10) Patent Number: US RE39,498 E
(45) Date of Reissued Patent: Feb. 27, 2007

(54) TREATMENT FOR CARDIOVASCULAR AND RELATED DISEASES

(75) Inventors: Karim Rouan Cham, Redland Bay (AU); Bill Elliot Cham, Sheldon (AU)

(73) Assignee: Aruba International Pty. Ltd. (AU)

(21) Appl. No.: 09/879,002

(22) PCT Filed: Dec. 22, 1995

(86) PCT No.: PCT/AU95/00875

§ 371 (c)(1),
(2), (4) Date: Jun. 10, 1997

(87) PCT Pub. No.: WO96/19250

PCT Pub. Date: Jun. 27, 1996

Related U.S. Patent Documents

Reissue of:
(64) Patent No.: 5,911,698
Issued: Jun. 15, 1999
Appl. No.: 08/849,543
Filed: Jun. 10, 1997

(30) Foreign Application Priority Data

Dec. 22, 1994 (AU) ..... PN 0307

(51) Int. Cl.
*A61M 37/00* (2006.01)
*A61M 1/36* (2006.01)
*B01D 11/00* (2006.01)
*C02F 1/44* (2006.01)

(52) U.S. Cl. ..... 604/5.03; 604/4.01; 422/44; 210/645; 210/651

(58) Field of Classification Search ..... 604/4.01, 604/5.01–5.04, 6.01, 85; 422/44; 210/645, 210/650–1, 767, 749, 348, 634, 502.1; 530/422, 530/850, 412–424, 539, 827, 829–830; 435/5; 424/9.1, 520, 529–531; 436/71
See application file for complete search history.

(56) References Cited

U.S. PATENT DOCUMENTS

| | | | |
|---|---|---|---|
| 3,647,624 | A | 3/1972 | Evenson |
| 3,958,939 | A | 5/1976 | Jones |
| 3,983,008 | A | 9/1976 | Shinozaki et al. |
| 3,989,466 | A | 11/1976 | Pan |
| 4,025,423 | A | 5/1977 | Stönner et al. |
| 4,103,685 | A | 8/1978 | Lupien et al. |
| 4,124,509 | A | 11/1978 | Iijima et al. |
| 4,234,317 | A | 11/1980 | Lucas et al. |
| 4,235,602 | A | 11/1980 | Meyer et al. |
| 4,258,010 | A | 3/1981 | Rözsa et al. |
| 4,350,156 | A | 9/1982 | Malchesky et al. |
| 4,391,711 | A | 7/1983 | Jackson et al. |
| 4,399,217 | A | 8/1983 | Holmquist et al. |
| 4,402,940 | A | 9/1983 | Nose et al. |
| 4,435,289 | A | 3/1984 | Breslau |
| 4,463,988 | A | 8/1984 | Bouck et al. |
| 4,481,189 | A | 11/1984 | Prince |
| 4,522,809 | A | 6/1985 | Adamowicz et al. |
| 4,540,401 | A | 9/1985 | Marten |
| 4,540,573 | A | 9/1985 | Neurath et al. |
| 4,581,231 | A | 4/1986 | Purcell et al. |
| 4,591,505 | A | 5/1986 | Prince |
| 4,613,501 | A | 9/1986 | Horowitz |
| 4,615,886 | A | 10/1986 | Purcell et al. |
| 4,643,718 | A | 2/1987 | Marten |
| 4,645,512 | A | 2/1987 | Johns |
| 4,647,280 | A | 3/1987 | Maaskant et al. |

(Continued)

FOREIGN PATENT DOCUMENTS

| | | | |
|---|---|---|---|
| CA | 1 271 708 | | 7/1990 |
| CN | 1189378 | | 8/1998 |
| DE | 29 44 138 | A1 | 6/1981 |
| DE | 31 18072 | A1 | 11/1982 |
| DE | 32 13390 | A1 | 10/1983 |
| DE | 33 10 263 | A1 | 9/1984 |
| EP | 0 036 283 | A2 | 3/1981 |
| EP | 0 267 471 | A1 | 10/1987 |
| FR | 2 571 971 | | 10/1984 |
| JP | 127104 | | 10/1980 |
| JP | 277303 | | 10/1993 |
| SU | 1116396 | A | 9/1984 |
| SU | 1204224 | A | 1/1986 |
| SU | 1752187 | A3 | 7/1992 |
| WO | WO 88/09345 | A1 | 12/1988 |
| WO | WO 95/03840 | * | 2/1995 |
| WO | WO 9503840 | A1 | 2/1995 |

OTHER PUBLICATIONS

Agnese, S.T. et al. , "Evaluation of Four Reagents for Delipidation of Serum", Clinical Biochemistry, 16(2): pp. 98–100 (1983).

(Continued)

*Primary Examiner*—Patricia Bianco
(74) *Attorney, Agent, or Firm*—Kilpatrick Stockton LLP

(57) ABSTRACT

A method for the removal of cholesterol, triglycerides and other lipids from animal plasma, serum or other suitable blood fractions, as a discontinuous flow system, the method comprising withdrawing blood from a subject, separating the required fraction from the blood and mixing with a solvent mixture which extracts the lipids from the fraction, after which the delipidated fraction is recombined with the blood cells and returned to the subject, wherein the solvent extraction step is carried out separately and remote from the subject. The delipidated fraction is washed with a second solvent before being recombined with the blood cells. To ensure that the delipidated fraction is free from all extraction solvent, the fraction is mixed with an absorbent specific for the solvent that is being removed. The preferred absorbent is a macroporous polymeric bead contained in the pores of a sintered glass or plastic sphere, the being capable of absorbing organic molecules from an aqueous solution. By treating the plasma, serum or other suitable blood fraction of a patient by these methods, the blood rheology of a patient with impaired blood circulation can be improved. Further, a rapid regression of coronary atherosclerosis occurs.

47 Claims, No Drawings

U.S. PATENT DOCUMENTS

| | | | | |
|---|---|---|---|---|
| 4,648,974 | A | * | 3/1987 | Rosskopf et al. |
| 4,668,398 | A | | 5/1987 | Silvis |
| 4,671,909 | A | | 6/1987 | Torobin |
| 4,676,905 | A | | 6/1987 | Nagao et al. |
| 4,677,057 | A | | 6/1987 | Curtiss et al. |
| 4,680,320 | A | | 7/1987 | Uku et al. |
| 4,696,670 | A | | 9/1987 | Ohnishi et al. |
| 4,775,483 | A | | 10/1988 | Mookerjea et al. |
| 4,832,034 | A | | 5/1989 | Pizziconi et al. |
| 4,836,928 | A | | 6/1989 | Aoyagi et al. |
| 4,879,037 | A | | 11/1989 | Utzinger |
| 4,895,558 | A | * | 1/1990 | Cham |
| 4,908,354 | A | * | 3/1990 | Seidel et al. |
| 4,909,940 | A | | 3/1990 | Horowitz et al. |
| 4,909,942 | A | | 3/1990 | Sato et al. |
| 4,923,439 | A | | 5/1990 | Seidel et al. |
| 4,935,204 | A | * | 6/1990 | Seidel et al. |
| 4,966,709 | A | | 10/1990 | Nosé et al. |
| 4,970,144 | A | | 11/1990 | Fareed et al. |
| 5,026,479 | A | | 6/1991 | Bikson et al. |
| 5,080,796 | A | | 1/1992 | Nosé et al. |
| 5,089,602 | A | | 2/1992 | Isliker et al. |
| 5,112,956 | A | | 5/1992 | Tang et al. |
| 5,116,307 | A | | 5/1992 | Collins |
| 5,126,240 | A | | 6/1992 | Curtiss |
| 5,128,318 | A | | 7/1992 | Levine et al. |
| 5,152,743 | A | | 10/1992 | Gorsuch et al. |
| 5,187,010 | A | | 2/1993 | Parham et al. |
| 5,203,778 | A | | 4/1993 | Boehringer et al. |
| 5,211,850 | A | | 5/1993 | Shettigar et al. |
| 5,236,644 | A | | 8/1993 | Parham et al. |
| 5,256,767 | A | | 10/1993 | Salk et al. |
| 5,258,149 | A | | 11/1993 | Parham et al. |
| 5,279,540 | A | * | 1/1994 | Davidson |
| 5,301,694 | A | | 4/1994 | Raymond et al. |
| 5,354,262 | A | | 10/1994 | Boehringer et al. |
| 5,391,143 | A | | 2/1995 | Kensey |
| 5,393,429 | A | | 2/1995 | Nakayama et al. |
| 5,401,415 | A | * | 3/1995 | Rauh et al. |
| 5,401,466 | A | | 3/1995 | Foltz et al. |
| 5,418,061 | A | | 5/1995 | Parham et al. |
| 5,419,759 | A | | 5/1995 | Naficy |
| 5,424,068 | A | * | 6/1995 | Filip |
| 5,476,715 | A | | 12/1995 | Otto |
| 5,484,396 | A | | 1/1996 | Naficy |
| 5,496,637 | A | | 3/1996 | Parham et al. |
| 5,523,096 | A | | 6/1996 | Okarma et al. |
| 5,634,893 | A | | 6/1997 | Rishton |
| 5,637,224 | A | | 6/1997 | Sirkar et al. |
| 5,652,339 | A | | 7/1997 | Lerch et al. |
| 5,679,260 | A | * | 10/1997 | Boos et al. |
| 5,698,432 | A | | 12/1997 | Oxford |
| 5,707,673 | A | | 1/1998 | Prevost et al. |
| 5,719,194 | A | | 2/1998 | Mann et al. |
| 5,744,038 | A | | 4/1998 | Cham |
| 5,753,227 | A | | 5/1998 | Strahilevitz |
| 5,853,725 | A | | 12/1998 | Salk et al. |
| 5,855,782 | A | | 1/1999 | Falkenhagen et al. |
| 5,858,238 | A | | 1/1999 | McRea et al. |
| 5,877,005 | A | | 3/1999 | Castor |
| 5,885,578 | A | | 3/1999 | Salk et al. |
| 5,895,650 | A | | 4/1999 | Salk et al. |
| 5,911,698 | A | | 6/1999 | Cham |
| 5,916,806 | A | | 6/1999 | Salk et al. |
| 5,919,369 | A | | 7/1999 | Ash |
| 5,928,930 | A | | 7/1999 | Salk et al. |
| 5,948,441 | A | | 9/1999 | Lenk et al. |
| 5,962,322 | A | | 10/1999 | Kozarsky et al. |
| 5,980,478 | A | | 11/1999 | Gorsuch et al. |
| 6,017,543 | A | | 1/2000 | Salk et al. |
| 6,022,333 | A | | 2/2000 | Kensev |
| 6,037,458 | A | | 3/2000 | Hirai et al. |
| 6,039,946 | A | | 3/2000 | Strahilevitz |
| 6,193,891 | B1 | | 2/2001 | Kent et al. |
| 6,309,550 | B1 | | 10/2001 | Iverson et al. |

OTHER PUBLICATIONS

Albouz, S. et al. , "Extraction of Plasma Lipids Preserving Antigenic Properties of Proteins and Allowing Quantitation of Gangliosides by Neuraminic Acid Determination", Ann. Biol. Clin. (Paris) (4ZS), 37(5): pp. 287–290 (1979).

Badimon, J.J. et al. , "High Density Lipoprotein Plasma Fractions Inhibit Aortic Fatty Streaks in Cholesterol–Fed Rabbits", Laboratory Investigation, vol. 60, No. 3: pp. 455–461 (1989).

Badimon, J.J. et al. , "Regression of Atherosclerotic Lesions by High Density Lipoprotein Plasma Fraction in the Cholesterol–Fed Rabbit", J. Clinical Investigation, vol. 85, No. 4: pp. 1234–1241 (1990).

Cham, B.E., et al. , "A Solvent System for Delipidation of Plasma or Serum Without Protein Precipitation", J. of Lipid Research, vol. 17: pp. 176–181 (1976).

Cham, B.E. et al. , "Changes in Electrophoretic Mobilities of α–and β–Lipoproteins as a Result of Plasma Delipidation", Clinical Chemistry, 22: pp. 305–309 (1976).

Cham, B.E., et al., "Heterogeneity of Lipoprotein B", Biochemical and Biophysical Research Communications, vol. 103, No. 1: pp. 196–206 (1981).

Cham, B.E., et al. , "Importance of Apolipoproteins in Lipid Metabolism", Chem. Biol. Interactions, 20: pp. 263–277 (1978).

Cham, B.E. et al. , "In Vitro Partial Relipidation of Apolipoproteins in Plasma", J. Biol. Chem., 251 (20): pp. 6367–6371 (1976).

Cham, B.E., et al., "Lipid Apheresis in an Animal Model Causes Acute Reduction in Plasma Lipid Concentrations and Mobilisation of Lipid from Liver and Aorta", Pharmacol. (Life Sci. Adv.)13: pp. 25–32 (1994).

Cham, B.E., et al. , "Lipid Apheresis in an Animal Model Causes In Vivo Changes in Lipoprotein Electrophoretic Patterns", J. Clin. Apheresis, 11 (2): pp. 61–70 (1996).

Cham, B.E., et al. , "Lipid Apheresis: An In Vivo Application of Plasma Delipidation with Organic Solvents Resulting in Acute Transient Reduction of Circulating Plasma Lipids in Animals", J. Clin. Apheresis 10: pp. 61–69 (1995).

Cham, B.E., Nature of the Interaction Between Low–Density Lipoproteins and Polyanions and Metal Ions, as Exemplified by Heparin and $Ca^{2+}$, Clinical Chemistry, vol. 22, No. 11: pp. 1812–1816 (1976).

Cham, B.E., et al., "Phospholipids in EDTA—Treated Plasma and Serum", Clinical Chemistry, vol. 39, No. 11: pp. 2347–2348 (1993).

Cham, B.E., et al., "Rapid Regression of Atherosclerosis by Cholesterol Apheresis—A Newly Developed Technique", 59$^{th}$ Congress European Atherosclerosis Society, Nice France, May 17–21, 1992.

Cham, B.E., et al., "Rapid, Sensitive Method for the Separation of Free Cholesterol from Ester Cholesterol", Clinica Chimica Acta, 49: pp. 109–113 (1973).

Dwivedy, A.K., "Increase of Reverse Cholesterol Transport by Cholesterol Apheresis: Regression of Atherosclerosis", 18$^{th}$ Australian Atherosclerosis Society Conference, Surfers Paradise, p. 21 (1992).

Eisenhauer, T. et al. , "Selective Removal of Low Density Lipoproteins (LDL) by Precipitation at Low pH: First Clinical Application of the HELP System", Klin Wochenschr (KWH), 65 (4): pp. 161–168 (1987).

Fang, N.X. et al. , "In vivo Rapid Mobilization of Adipose Tissue by Lipid Apheresis—A Newly Developed Technique", 18$^{th}$ Australian Atherosclerosis Society Conference, Gold Cost, Australia 1992.

Innerarity, T.L., et al. , "Enhanced Binding by Cultured Human Fibroblasts of Apo–E–Containing Lipoproteins as Compared with Low Density Lipoproteins", Biochemistry, vol. 17: pp. 1440–1447 (1978).

Koizumi, J. et al. , "Behavior of Human Apolipoprotein A–1: Phospho–Lipid and apoHDL: Phospholipid Complexes in Vitro and After Injection into Rabbits", J. Lipid Research, vol. 29: 1405–1415 (1988).

Kostner, K. et al., "Increase of APO A1 Concentration in Hypercholesteraemic Chickens After Treatment with a Newly Developed Extracorpreal Lipid Elimination", XI Internet Symp. On Drugs Affecting Lipid Metabolism, Italy, May 13–16, 1992.

Kostner, K. et al., "Lecithin–cholesterol acyltransferase activity in Normocholesterolaemic and Hypercholesterolaemic Roosters: Modulation by Lipid Apheresis", European Journal of Clinical Investigation, vol. 27; pp. 212–218, May 7, 1997.

Lupien, P.J. et al., "A New Approach to the Management of Familial Hypercholesterolaemia: Removal of Plasma–Cholesterol Based on the Principle of Affinity Chromatography", Lancet (LOS), 1 (7972)L: pp. 1261–1265 (1976).

Parker, T.S., et al., "Plasma High Density Lipoprotein is Increased in Man When Low Density Lipoprotein (LDL) is Lowered by LDL–Pheresis"; Proc. Nat. Acad. Sci. (USA) 83(3), pp. 777–781 (1986) (Abstract).

Ryan, W.G. et al., "An Improved Extraction Procedure for the Determination of Triglycerides and Cholesterol in Plasma or Serum", Clinical Chemistry, vol. 13: pp. 769–772 (1967).

Slater, H.R. et al., "A Comparison of Delipidated Sera Used in Studies of Sterol Synthesis by Human Mononuclear Leukocytes", J. of Lipid Research, 20: pp. 413–416 (1979).

Slater, H.R. et al. , "The Effect of Delipidated High Density Lipoprotein on Human Leukocyte Sterol Synthesis", Atherosclerosis, 35: pp. 41–49 (1980).

Thompson, G.R. et al. , "Plasma Exchange in the Management of Homozygous Familial Hypercholesterolaemia", Lancet (LOS, 1 (7918): pp. 1208–1211 (1975).

Williams, K.J. et al., "Low Density Lipoprotein Receptor–Independent Hepatic Uptake of a Synthetic, Cholesterol–Scavenging Lipoprotein: Implications for the Treatment of Receptor–Deficient Atherosclerosis", Proc. Natl. Acad. Sci. USA, vol. 85: pp. 242–246 (1988).

Yokoyama, S. et al., "Selective Removal of Low Density Lipoprotein by Plasmapheresis in Familial Hypercholesterolemia", Arteriosclerosis (89S), 5 (6): pp. 613–622 (1985).

Parker, Thomas S. et al. , "Plasma High Density Lipoprotein is Increased in Man When Low Density Lipoprotein (LDL) is Lowered by LDL–Pheresis", Proceedings of the National Academy of Sciences, vol. 83, pp. 777–781 (1986).

Bloom, et al. "Quantitation of lipid profiles from isolated serum lipoproteins using small volumes of human serum." Clin Biochem 1981 Jun;14(3): 119–25.

Wong, et al. "Retention of gangliosides in serum delipidated by diisopropyl ether–1–butanol extraction," Journal of Lipid Research, 1983, 24, 666–669.

Klimov, et al. "Extraction of Lipids from Blood Plasma and Subsequent Introduction of Autologous Delipidized Plasma into the Body as a Possible Means to Treat Artherosclerosis," English translation from the Russian Journal Kardiologiia, 1978, 18(6): 23–29.

Asztalos et al., Arterioscler. Thromb. Vasc. Biol., Presence and Formation of 'Free Apolipoprotein A–I–Like' Particles in Human Plasma, 15, 1419–1423,. (1995).

Asztalos et al., Arterioscler. Thromb. Vasc. Biol., Role of Free Apolipoprotein A–I in Cholesterol Efflux, 17, 1630–1636. (1997).

Barrans et al., Biochimica et Biophysica Acta, Pre–β HDL: Structure and Metabolism, 1300, 73–85. (1996).

Collet et al., Journal of Biological Chemistry, Differential Effects of Lecithin and Cholesterol on the Immunoreactivity and Confirmation of Apolipoprotein A–I in High Density Lipoproteins, 266 (14), 9145–9152. (May 15, 1991).

Cruzado et al., Analytical Biochemistry, Characterization and Quantitation of the Apoproteins of High–Density Lipoprotein by Capillary Electrophoresis, 14 (7), 100–109. (1996).

Deva, et al., J. Hosp. Infect., Establishment of an in–use testing method for evaluating disinfection of surgical instruments using the duck hepatitis B model , 22, 119–130. (abstract only) (Jun. 1996).

Feinstone, et al., Infection and Immunity, Inactivation of Hepatitis B Virus and Non–A, Non–B Hepatitis by Chloroform, 41, 816–821. (Aug. 1983).

Hatch et al., Lipoprotein Analysis, Advances in Lipid Research, Practical Methods for Plasma Lipoprotein Analysis, 6, 1–68. (1968).

Horowitz, et al., Blood Coagulation and Fibrinolysis, Viral safety of solvent/detergent–treated blood products, 5, S21–S28. (1994).

Jackson et al., Biochimica et Biophysica Acta, Isolation and Characterization of the Major Apolipoprotein from Chicken High Density Lipoproteins, 420, 342–349. (1976).

Koudinov et al., Cell Biol Int., Alzheimer's Soluble Amyloid Beta Protein is Secreted by HepG2 Cells as an Apolipoprotein, 21 (5), 265–71. (abstract only) (May 1997).

Moya et al., Arteriosclerosis and Thrombosis, A Cell Culture System for Screening Human Serum for Ability to Promote Cellular Cholesterol Efflux, 14 (7), 1056–1065. (Jul. 1994).

Ngu, Medical Hypotheses, Chronic Infections from the Perspective of Evolution: a Hypothesis, 42, 81–88. (1994).

Ngu, Medical Hypotheses, Human Cancers and Viruses: A Hypothesis for Immune Destruction of Tumours Caused by Certain Enveloped Viruses Using Modified Viral Antigens, 39, 17–21. (1992).

Ngu, Medical Hypotheses, The viral envelope in the evolution of HIV: a hypothetical approach to inducing an effective immune response to the virus, 48, 517–521. (1997).

Okazaki et al., Journal of Chromatography, Biomedical Applications, Improved High–Performance Liquid Chromatographic Method for the Determination of Apolopoproteins in Serum High–Density Lipoproteins, 430, 135–142. (1988).

Robern et al., Experientia, The Application of Sodium Deoxycholate and Sephacryl–200 for the Delipidation and Separation of High Density Lipoproteins, 38, 437–439. (1982).

Scanu et al., Analytical Biochemistry, Solubility in Aqueous Solutions of Ethanol of the Small Molecular Weight Peptides of the Serum Very Low Density and High Density Lipoproteins: Relevance to the Recovery Problem During Delipidation of Serum Lipoproteins, 44, 576–588. (1971).

Williams et al., Biochim. Biophys. Act., Uptake of Endogenous Cholesterol by a Synthetic Lipoprotein , 875 (2), 183–194. (Feb. 12, 1986).

* cited by examiner

TREATMENT FOR CARDIOVASCULAR AND RELATED DISEASES

Matter enclosed in heavy brackets [ ] appears in the original patent but forms no part of this reissue specification; matter printed in italics indicates the additions made by reissue.

CROSS-REFERENCE TO RELATED APPLICATION

This application is a U.S. National Phase Application filed under 35 U.S.C. § 371 based on International Application No. PCT/AU95/00875, having an International Filing Date of Dec. 22, 1995.

TECHNICAL FIELD

THIS INVENTION relates to plasma or serum delipidation in animals (which term shall indicate humans), to a treatment for cardiovascular disease and to removal of excess fat from the animals. In particular, it is directed to the removal of cholesterol, triglycerides and other lipids, and fat soluble toxins—for example, insecticides—from the blood plasma or serum of such animals.

BACKGROUND ART

Cardiovascular diseases are responsible for a significant number of deaths in most industrialised countries.

One such disease is atherosclerosis which is characterised by local fatty thickening in the inner aspects of large vessels supplying blood to the heart, brain and other vital organs. These lesions obstruct the lumen of the vessel and result in ischaemia of the tissue supplied by the vessel. Prolonged or sudden ischaemia may result in a clinical heart attack or stroke from which the patient may or may not recover.

The relationship between dietary lipid, serum cholesterol and atherosclerosis has long been recognised. In many epidemiological studies it has been shown that a single measurement of serum cholesterol has proved to be a significant predictor of the occurrence of coronary heart disease.

Thus diet is the basic element of all therapy for hyperlipidaemia (excessive amount of fat in plasma). However, the use of diet as a primary mode of therapy requires a major effort on the part of physicians, nutritionists, dieticians and other health professionals.

If dietary modification is unsuccessful, drug therapy is an alternative. Several drugs, used singly or in combination, are available. However, there is no direct evidence that any cholesterol-lowering drug can be safely administered over an extended period.

A combination of both drug and diet may be required to reduce the concentration of plasma lipids. Hypolipidaemic drugs are therefore used as a supplement to dietary control.

Many drugs are effective in reducing blood lipids, but none work in all types of hyperlipidaemia and they all have undesirable side effects. There is no conclusive evidence that hypolipidaemic drugs can cause regression of atherosclerosis. Thus, despite progress in achieving the lowering of plasma cholesterol to prevent heart disease by diet, drug therapies, surgical revascularization procedures and angioplasty, atherosclerosis remains the major cause of death in Western Countries.

In view of the above, new approaches have been sought to reduce the amount of lipid in the plasma of homozygotes and that of heterozygotes for whom oral drugs are not effective.

Plasmapheresis (plasma exchange) therapy has been developed and involves replacement of the patient's plasma with donor plasma or more usually a plasma protein fraction. This treatment can result in complications due to the possible introduction of foreign proteins and transmission of infectious diseases. Further, plasma exchange removes all the plasma proteins as well as very low density lipoprotein (VLDL), low density lipoprotein (LDL), and high density lipoprotein (HDL).

It is known that HDL is inversely correlated with the severity of coronary arterial lesions as well as with the likelihood that these will progress. Therefore, removal of HDL is not advantageous.

Known aphaeresis techniques also exist which can remove LDL from plasma. These techniques include absorption of LDL in heparinagarose beads (affinity chromatography) or the use of immobilised LDL-antibodies. Other methods presently available for the removal of LDL involve cascade filtration absorption to immobilised dextran sulphate and LDL precipitation at low pH in the presence of heparin. Each method specifically removes LDL but not HDL.

LDL aphaeresis has, however, disadvantages. Significant amounts of other plasma proteins are removed during aphaeresis and to obtain a sustained reduction in LDL-cholesterol, LDL aphaeresis must be performed frequently (up to once weekly). Furthermore, LDL removal may be counter productive as, low blood LDL levels may result in increased cellular cholesterol synthesis.

To satisfy the need for a method of achieving a reduction in plasma cholesterol in homozygous familial hypercholesterolemia, heterozygous familial hypercholesterolemia and patients with acquired hyperlipidaemia other than by diet, drug therapy, LDL aphaeresis, or a combination of these, an extra corporeal lipid elimination process, termed "cholesterol aphaeresis", has been developed. In cholesterol aphaeresis, blood is withdrawn from a subject, plasma separated from the blood and mixed with a solvent mixture which extracts lipid from the plasma, after which the delipidated plasma is recombined with the blood cells and returned to the subject.

In more detail, cholesterol aphaeresis results in the removal of fats from plasma or serum. However, unlike LDL aphaeresis, the proteins that transport the fat (apolipoproteins) remain soluble in the treated plasma or serum. Thus the apolipoproteins of VLDL, LDL and HDL are present in the treated plasma or serum. These apolipoproteins, in particular apolipoproteins A1 from the defatted HDL in the plasma or serum, are responsible for the mobilisation of excessive amounts of deposited fats such as cholesterol in arteries, plaques, or excessive amounts of triglycerides, adipose tissue, or fat soluble toxins that are present in adipose tissue. These excessive amount of fats or toxins are transferred to the plasma or serum, bound to the newly assembled lipoproteins. Thus by applying another cholesterol aphaeresis procedure, these unwanted fats or toxins are successively removed from the plasma and thus the body.

The main advantage of this procedure is that LDL and HDL are thus not removed from the plasma but only cholesterol, some phospholipids and considerable triglycerides. U.S. Pat. No. 4,895,558 describes such a system.

While cholesterol aphaeresis has overcome the shortcomings of dietary and/or drug treatments and other aphaeretic techniques, existing apparatus for cholesterol aphaeresis does not provide a sufficiently rapid and safe process. For use in a clinical setting, apparatus is required which effects delipidation more efficiently. Furthermore, flow rates of the order of 70 ml/min are required for cholesterol aphaeresis of a human subject.

Thus the cholesterol aphaeresis described in the aforementioned U.S. Pat. No. 4,895,558 was improved by incorporating into the system a spinner to disperse the incoming plasma laterally into the extracting solvent in the form of fine droplets to improve separation efficiency. This improved system is described in International Patent Application No. PCT/AU94/00415.

Unfortunately, practice has established that the cholesterol aphaeresis systems described above still suffer from a number of disadvantages.

The first disadvantage is the explosive nature of the solvents used to delipidate this plasma. These solvents are, by the very nature of the continuous systems, in close proximity to the patient and medical staff. This hazard is clearly present for the duration of the delipidation process which usually runs for several hours.

The second disadvantage is that, in the prior continuous systems, a reliable procedure is not available to remove totally all of the solvents used in the delipidation before the treated plasma is returned to the patient.

In particular, the use of the preferred solvent 1-butanol in the delipidation is of concern as it can now be established that that solvent can be present as 1% to 5% of the treated plasma that is returned to the patient. This is because continuous systems can only include a single wash to remove solvents such as 1-butanol and a single wash is now found to be sufficient. It is not possible to provide sequential multi-washes in a continuous system because the patient would have to supply an unacceptable volume of blood to maintain each stage of the system overall and the patient would also be subjected to an increased hazard factor from the prolonged exposure to the solvents.

The long term toxicity of 1-butanol is not known, especially when directly present in the blood stream—it may cross the blood brain barrier. Certainly, external contact with this solvent is known to cause irritation of mucous membranes, contact dermatitis, headaches, dizziness and drowsiness.

A third disadvantage is that the continuous systems described above are not suitable for the delipidation of serum. If serum can be delipidated, there would be the advantage of favourably altering the blood rheology in that the viscosity will decrease following delipidation resulting in better haemodynamics for the originally impaired blood circulation.

Yet a fourth disadvantage is that delipidation in a continuous system is undertaken over several hours. Apart from the prolonged exposure to the hazardous solvents as discussed above, the equipment and staff are committed to a single patient. As the removal of plasma or other blood fractions and their subsequent return to the patient as individual steps each only take a few minutes, it would be advantageous if the relatively lengthy delipidation step could be undertaken off site, thus freeing the patient, medical staff and equipment for other matters.

Finally, in a continuous system, clearly it is only the patient's own blood fraction that can be returned to that patient. However, for example, if the patient's plasma or serum could be removed and treated remote from the patient, then either autologous or non-autologous plasma or serum could be returned to the patient at a later date.

SUMMARY OF THE INVENTION

It is an object of the present invention to overcome, or at least ameliorate, the above-mentioned disadvantages in the provision of a method for delipidating not only plasma but also serum and other blood fractions which substantially reduces the exposure of the patient to the potentially hazardous solvents used, which also can effectively remove all traces of solvent(s) used in that delipidation, and which significantly reduces the contact time between the patient and the actual delipidation process.

It is a further object to provide a method whereby advantageous changes to the blood rheology of the originally impaired blood circulation of the patient can be achieved.

It is yet another object to provide a method whereby a patient's Plasma or serum can be treated remote from that patient, thus allowing either autologous or non-autologous plasma or serum to be returned to the patient at a later date.

In one aspect of the present invention, there is provided a method for the removal of cholesterol, triglycerides and other lipids from animal plasma, serum or other suitable blood fractions, as a discontinuous flow system, said method comprising withdrawing blood from a subject, separating the required fraction from the blood and mixing with a solvent mixture which extracts the said lipids from the fraction, after which the delipidated fraction is recombined with the blood cells and returned to the subject, characterised in that the solvent extraction step is carried out separately and remote from the subject.

Preferably, as part of the solvent extraction step, beads are used when mixing the blood fractions with the solvent. More preferably, the beads have a density substantially mid-way between the density of the fraction and the density of the solvent mixture. This ensures efficient mixing with a large surface area, increasing the efficiency of the extraction and also serving as a good separator of the plasma from the solvent when centrifugation is used to isolate the phases after extraction.

Preferably, to obtain a density substantially mid-way between the density of the fraction and the density of the solvent mixture, the beads contain entrapped air.

More preferably, as the density of plasma is approximately 1.006 g/ml and the solvents used generally have a density of approximately 0.8 g/ml, the density of the beads will be around 0.9 g/ml.

The beads may be manufactured from any acceptable material such as glass or plastic.

Once the resultant delipidated fraction-containing phase has been isolated, all traces of the extraction solvent must be removed before the fraction is recombined with the blood cells and/or returned to the subject.

One way of removing this solvent is to wash with another solvent, preferably diethyl ether, to remove substantially all of the original solvent used in the extraction step.

More preferably, four (4) washes are undertaken.

However, as another aspect of the present invention, efficient removal of the extraction solvent can be achieved by mixing the delipidated fraction with an absorbent specific for the solvent that is being removed.

In particular, the absorbent is contained in the pores of sintered spheres.

More preferably, the sintered spheres are approximately 2 to 5 mm in diameter with the pores of the spheres being less than 50 Å in diameter. Most preferably, the spheres are manufactured from glass.

Preferably, the absorbents used in the sintered spheres are the macroporous polymeric beads for absorbing organic molecules from aqueous solutions marketed by Bio-Rad Laboratories under the trade name Bio-Beads SM.

If the solvent used to delipidate the fraction is 1-butanol, then the absorbent is preferably Bio-Beads SM-2.

Preferably, the absorbent is held in a chamber which is adapted to allow the delipidated fraction to pass through or over the absorbent at least twice if a single pass is insufficient to remove all of the solvent.

Preferably, as part of isolating the delipidated fraction-containing phase, that phase is subsequently washed with another solvent, preferably diethyl ether, to remove a substantial amount of the original solvent before the treatment with the absorbent.

More preferably, that phase is washed at least three (3) times.

The plasma may be human plasma or plasma from other living animals. The plasma can be obtained from human or animal blood by known plasma separating techniques which include centrifugal separation, filtration and the like.

Similarly, the serum or other lipid-containing fraction can be derived from human or other living animals by known techniques.

Suitable solvents for the extraction comprise mixtures of hydrocarbons, ethers and alcohols. Preferred solvents are mixtures of lower alcohols with lower ethers. The lower alcohols suitably include those which are not appreciably miscible with the plasma and these can include the butanols (butan-1-ol and butan-2-ol). $C_{1-4}$ ethers are also preferred and these can include the propyl ethers (di-isopropyl ether and propyl ether). Other solvents which may be applicable include amines, esters, hydrocarbons and mixtures providing that the solvent can (1) rapidly and preferably remove cholesterol from the plasma, (2) is substantially immiscible with the plasma, (3) can be removed from the plasma, and (4) does not denature the desired moieties. Preferred solvent compositions are butanol with di-isopropyl ether and these may be in the ratio of 0%–40% of the alcohol to 100%–60% of the ether.

DETAILED DESCRIPTION OF EMBODIMENTS

Materials and Methods

Animals

The roosters used in this study were of White Leghorn Hiline strain and were obtained as one-day old chicks. All roosters from 8 weeks old were transferred into individual cages. Water and feed were supplied unrestricted. At eight weeks of age, 15 control birds were fed a commercial poultry ration for 31 days and another group of 30 birds were injected subcutaneously each day with 5 mg diethylstilboestrol (DES) in sesame oil for a period of 31 days. In addition they were fed on the same commercial diet which was supplemented with 2.6% (w/w) cholesterol for a period of 31 days. Fifteen animals of the DES treated group were then subjected to lipid aphaeresis (LA). Fifteen animals of the DES treated group had sham treatments. Once the LA or sham treatments commenced, all animals were fed the standard poultry ration, except during the actual treatment itself when animals were kept off their feed for three hours following reinfusion of their autologous blood. Animals were sacrificed two days following the 4th treatment, LA or sham.

Lipid Aphaeresis Procedure

Approximately 25% of the calculated blood volume was collected from a brachial vein of the animal with a 21 gauge needle and syringe. The total blood volume was estimated at 8 percent of the body weight. The blood was collected in heparinized tubes and immediately centrifuged at 900 g for 5 minutes at room temperature. The blood cells were suspended in an amount of saline equivalent to the plasma volume and were reinfused into the animal. The plasma was kept refrigerated for twelve hours and was then delipidated for 20 minutes with a mixture of butanol and di-isopropyl ether (DIPE), 25:75 (v/v), in a ratio of one volume of plasma to two volumes of butanol-DIPE mixture (organic phase). Inert plastic beads with a density of 0.9 g/mL (1 g) were added to the mixture. After extraction, the mixture was centrifuged at 900 g for 2 min to separate the plasma and organic phases. The organic phase (upper layer) was removed, free of plasma phase, by careful aspiration with a pasteur pipette under vacuum. Traces of butanol in the plasma phase were washed out with four volumes of diethyl ether (DEE) for 2 min by end-over-end rotation at 30 rpm. The mixture was then centrifuged at 900 g for 2 min to separate plasma and ether phases. The ether phase was subsequently removed by aspiration with a pasteur pipette. Residual ether was removed by evacuation with a water pump aspirator at 37° C. The plasma was then passed through a 5 mL column containing Bio-Beads SM-2.

This procedure yielded delipidated plasma. The delipidated plasma was re-mixed with the blood cells of a subsequent 25% blood collection which was then reinfused through a brachial vein back into the identical donor animals. The duration of the entire procedure, that is, removal of blood from the animal to reinfusion of treated blood back to the animal was approximately 1 hour. After the fourth lipid aphaeresis treatment, the animals were sacrificed and their livers and aortae were dissected. The LA treatment procedures were repeated 3 times after the first treatment.

Sham Treatment Procedures

This was essentially the same as the LA procedure with the exception of the plasma delipidation with the organic solvents. The blood was collected in heparinized tubes and immediately centrifuged at 900 g for 5 min. The plasma was separated from the blood cells. The blood cells were mixed with saline in the same volume of the collected plasma and reinfused into the animal. The plasma was kept refrigerated for twelve hours and was then remixed with blood cells of a subsequent 25% blood collection after the second and/or subsequent plasma separations. After the fourth lipid aphaeresis treatment, the animals were sacrificed and their livers and aortae were dissected. The sham treatment procedures were repeated 3 times after the first treatment.

Tissue Lipid Preparation

The livers were weighed, minced with a scalpel blade and homogenised in 0.9% sodium chloride solution by 10–12 strokes of a motor driven Teflon-glass homogeniser (1900 rpm). The aorta was weighed and three times its weight of 3 mm glass beads were added in a homogenising bottle containing 0.9% sodium chloride. The contents were then homogenised for one minute. The lipid from the homogenised liver and aorta samples were extracted by the Folch procedure and weighed.

TABLE I

Effect of LA and sham treatments on the total lipid concentrations in livers and aortas of hyperdiedemic roosters

| | UNTREATED | TREATED FOUR APHAFRESIS APPLICATIONS | |
|---|---|---|---|
| | CONTROLS n = 15 | SHAM n = 15 | LA n = 15 |
| LIVER[a] | 3.65 ± 0.98 | 5.53 ± 1.50[b] | 3.72 ± 1.00[2] |
| AORTA[c] | 6.01 ± 0.97 | 0.11 ± 2.15[c] | 0.32 × 0.95[d] |

[a]Total lipid concentrations expressed as g lipid per 100 g tissue, mean ± SD

[b,c]p values were <0.05 when sham treatments were compared with LA treatments.

There were no statistical differences between the values of corresponding tisues in the untreated control group and the LA treated group.

All animals were sacrificed two days after the final apherical treatment.

Humans

Patients have the plasmapheresis procedure undertaken using known transvenous techniques and plasmapheresis systems.

Plasmapheresis is performed using vein-to-vein or arteriovenous fistula in the forearm of patients. Heparin is given at the beginning of the procedure as a 5,000 unit bolus, and then by continuous infusion at the rate of 700 units per hour over the course of the procedure. Access through the antecubital veins should provide plasma flow rates of 25 to 40 mls per minute.

Blood taken from a patient is immediately treated with ACD-A (anticoagulant) in a ratio of between 1:8 and 1:16 (ACD-A:blood). The plasma is separated from this solution using a conventional plasmapheresis machine.

Twenty five percent plasma is removed from the patient. This represents one percent of the ideal body weight.

Only the first volume of plasma collection is replaced with plasma replacement fluid to the patient.

The plasma is kept refrigerated up until twelve hours prior to reinfusion of delipidated plasma in exchange for another twenty five percent plasma collection (weekly or biweekly).

The plasma is delipidated and the delipidated plasma is tested to ensure all solvent has been removed before the clean delipidated plasma is exchanged for new untreated plasma.

In one embodiment of the present invention, the continuous flow system described in U.S. Pat. No. 4,895,558 (the entire content of which is included herein) is modified to a discontinuous system by removing the appropriate blood volume to be treated and subjecting that volume to delipidation at a site remote from the patient.

In another embodiment of the present invention, the continuous flow system described in International Patent Application No. PCT/AU94/00415 (the entire content of which is included herein) is modified to a discontinuous system by removing the appropriate blood volume to be a site remote from the patient before the plasma is dispersed into small droplets into the solvent by the dispersing means.

In either of the above embodiments, the extraction step can include, in accordance with the present invention, either multiple washing of the extracted phase and/or using an absorbent.

For example, the plasma is delipidated with a solvent mixture comprising 1-butanol and di-isopropyl ether. The delipidated fraction is then washed three (3) or four (4) times with diethyl ether. After the final wash, the diethyl ether is removed by centrifugation and vacuum extraction at 37° C. The sintered spheres containing Bio-Beads SM-2 are then mixed with the delipidated plasma to remove the final traces of 1-butanol.

Conclusions

DES administration to the roosters resulted in a significant amount of fat (lipid) accumulation in the livers and aortae.

Discontinuous LA treatments corresponding to approximately one plasma volume treated by four applications of 25% of plasma volume treated per time resulted in significant decreases in both hepatic and aortic lipids in hyperlipidaemic animals. Moreover, the LA treated hyperlipidaemic animals ended up with lipid values that were similar to control animals.

(i) These experiments show that excessive amounts of body fats in the form of adipose tissue (triglycerides) in the liver can be removed by LA; and (ii) regression of atherosclerosis occurs in the aorta by LA treatments.

Similar results can be expected for human patients.

By adapting the prior art methods to discontinuous flow systems, the present invention can remove or at least significantly reduce any danger to patients and medical staff from the explosive nature of the solvents employed.

Further, by using the improved solvent extraction methods of the present invention, all of the potentially poisonous extraction solvents can be removed before the treated blood is returned to the patient.

Also, the improved solvent extraction method of the present invention is not limited to plasma delipidation but also it is applicable to the delipidation of serum, thus providing advantageous changes to the blood rheology of the originally impaired blood circulation of the patient.

The present invention thus provides for a rapid regression of coronary atherosclerosis in a patient.

Finally, as the present invention is a discontinuous system, it is not essential to return the delipidated blood fraction immediately to the patient. It is already known that plasma or serum can be collected and stored under sterile conditions in a refrigerator or freezer for extended periods and that it can be returned safely to the patient within twelve (12) hours of breaking the sterile seal. Therefore, if necessary, reintroduction of the delipidated fraction can occur several weeks after it was first removed from the patient. This option leads to particular advantages such as, economies of scale when several patients have to be treated simultaneously, the freeing of medical staff and equipment for other duties, and the reduction in stress for the patient whom no longer has to be hooked up to a delipidation apparatus for several continuous hours. Further, it enables a bank of plasma or serum to be maintained which is free of any infection which can be delipidated and exchanged for a patient's plasma or serum as required. Of course, autologous or non-autologous plasma or serum could be returned to the patient under these conditions.

The embodiments are described by way of illustrative examples only and various changes and modifications may be made thereto without departing from the inventive concept as defined in the following claims.

We claim:

1. A method for the removal of cholesterol, triglycerides and other lipids from animal plasma, serum, or other suitable blood fraction containing apolipoproteins, as a discontinuous flow system, said method comprising connecting a subject to a device for withdrawing blood, withdrawing blood containing blood cells from the subject, separating said fraction from the blood cells and mixing with a solvent mixture which extracts said lipids from the fraction but which does not extract said apolipoproteins from the fraction, after which the delipidated fraction is recombined with the blood cells and returned to the subject, such that the [solve it] *solvent* extraction step is carried out separately and remote from the subject while the subject is not still connected to the device for withdrawing blood [frown] *from* the subject, wherein the extraction solvent is removed from the delipidated fraction by mixing the delipidated fraction with an absorbent specific for the extraction solvent and wherein the absorbent does not remove said apolipoproteins from the [delipilidated] *delipidated* fraction being returned to the subject.

2. A method as defined in claim 1, wherein the extraction solvent is substantially removed from the delipidated fraction by washing with a second solvent.

3. A method as defined in claim 2, wherein the delipidated fraction is washed four times.

4. A method as defined in claim 2, wherein the second solvent is diethyl ether.

5. A method as defined in claim 1, wherein the absorbent is contained in the pores of sintered spheres.

6. A method as defined in claim 5, wherein the sintered spheres are about 2 mm to 5 mm in diameter and the pores of the spheres are less than 50 [Å] *.ANG.* in diameter.

7. A method as defined in claim 1, wherein the absorbent is a macroporous polymeric bead for absorbing organic molecules from an aqueous solution.

8. A method as defined in any one of claim 1, wherein the absorbent is held in a chamber which is adapted to allow the delipidated fraction to pass through or over the absorbent at least twice.

9. A porous sintered sphere for use in a method as defined in claim 1, said sphere containing an absorbent in its pores.

10. A sintered sphere as defined in claim 9, wherein the absorbent is a macroporous polymeric bead for absorbing organic molecules from an aqueous solution.

11. A method of changing the blood rheology of an animal with impaired blood circulation whereby the plasma, serum or other suitable blood fraction of the animal has been treated by a method as defined in claim 1.

12. A method for rapid regression of coronary atherosclerosis in an animal whereby the plasma, serum or other suitable blood fraction from the animal is treated by a method as defined in claim 1.

13. A method of removing excessive adipose tissue from an animal whereby the plasma, serum or other suitable blood fraction from the animal is treated by a method as defined in claim 1.

14. A method of removing fat soluble toxins from an animal whereby the plasma, serum or other suitable blood fraction from the animal is treated by a method as defined in claim 1.

15. A method of changing the blood rheology of an animal whereby the plasma or serum of the animal is exchanged for non-autologous plasma or serum wherein said non-autologous plasma or serum has been treated by a method as defined in of claim 1.

16. A method of rapidly regressing coronary atherosclerosis in an animal whereby the plasma or serum of the animal is exchanged for non-autologous plasma or serum wherein said non-autologous plasma or serum has been treated by a method as defined in claim 1.

17. A method of removing excessive adipose tissue from an animal whereby the plasma or serum of the animal is exchanged for non-autologous plasma or serum wherein said non-autologous plasma or serum has been treated by a method as defined in claim 1.

18. A method of removing fat soluble toxins from an animal whereby the plasma or serum of the animal is exchanged for non-autologous plasma or serum wherein said non-autologous plasma or serum has been treated by a method as defined in claim 1.

19. A method for the removal of cholesterol, triglycerides and other lipids from animal plasma, serum, or other suitable blood fraction containing apolipoproteins, a discontinuous flow system, said method comprising connecting a subject to a device for withdrawing blood, withdrawing blood containing blood cells from the subject, separating said fraction from the blood cells and mixing with a solvent mixture which extracts said lipids from the fraction but which does not extract said apolipoproteins from the fraction, after which the delipidated fraction is is recombined with the blood cells and returned to the subject such that the solvent extraction step is carried out separately and remote from the subject while the subject is not still connected to the device for withdrawing blood from the subject, wherein the solvent extraction step comprises:

(a) mixing the solvent mixture containing the fraction with beads, said beads being of a density substantially mid-way between the density of the fraction and the density of the solvent mixture; and (b) isolating the thus delipidated fraction-containing phase.

20. A method as defined in claim 19, wherein the beads contain entrapped air to obtain the density substantially midway between the density of the fraction and the density of the solvent mixture.

21. A method as defined in claim 20, wherein the density of the beads is about 0.9 g/ml.

*22. A batch method for removing lipids from a volume of animal or human plasma, serum, or other suitable blood fraction containing apolipoproteins comprising:*

*providing the volume of animal or human plasma, serum, or other suitable blood fraction;*

*admixing the plasma, serum, or other suitable blood fraction with an extraction solvent which extracts the lipids from the plasma, serum, or other suitable blood fraction without extracting the apolipoproteins to form a delipidated fraction;*

*introducing an absorbent to the delipidated fraction to substantially remove the extraction solvent from the plasma, serum, or other suitable blood fraction; and*

*separating the absorbent from the delipidated fraction to form a apolipoprotein containing delipidated fraction.*

*23. A batch method as claimed in claim 22, wherein the extraction solvent is substantially removed from the delipidated fraction by washing at least once with a second solvent.*

*24. A batch method as claimed in claim 22, wherein the extraction solvent is substantially removed from the delipidated fraction by washing a plurality of times with a second solvent.*

*25. A batch method as claimed in claim 23, wherein the second solvent is diethyl ether.*

*26. A batch method as claimed in claim 22, wherein the absorbent is disposed in the pores of sintered spheres.*

*27. A batch method as claimed in claim 26, wherein the pores of the sintered spheres are less than 50 Å in diameter.*

*28. A batch method as claimed in claim 22, wherein the absorbent is a macroporous polymeric bead for absorbing organic molecules from an aqueous solution.*

*29. A batch method as claimed in claim 22, wherein the absorbent is held in a chamber which is adapted to allow the delipidated fraction to pass through or over the absorbent at least twice.*

*30. A batch method as claimed in claim 22, further comprising:*

*mixing the apolipoprotein containing delipidated fraction with blood cells derived from an animal or a human to form a treated blood.*

*31. A batch method as claimed in claim 30, further comprising:*

*introducing the treated blood into the blood stream of an animal or a human, wherein the apolipoprotein containing delipidated fraction and the blood cells are respectively autologous or non-autologous to the animal or human.*

*32. A batch method as claimed in claim 22, further comprising:*

*introducing the apolipoprotein containing delipidated fraction into the blood stream of an animal or a human, wherein the apolipoprotein containing delipidated fraction is autologous or non-autologous to the animal or human.*

*33. A method of changing the blood rheology of an animal or a human with impaired blood circulation whereby the plasma, serum, or other suitable blood fraction of the animal or the human has been treated by a method as claimed in claim 31.*

*34. A method for rapid regression of coronary atherosclerosis in an animal or a human whereby the plasma, serum, or other suitable blood fraction from the animal or human is treated by a method as claimed in claim 31.*

*35. A method of removing excessive adipose tissue from an animal or a human whereby the plasma, serum or other suitable blood fraction from the animal or human is treated by a method as claimed in claim 31.*

*36. A method of removing fat soluble toxins from an animal or a human whereby the plasma, serum or other suitable blood fraction from the animal or human is treated by a method as claimed in claim 31.*

*37. A method of changing the blood rheology of an animal or a human whereby the plasma or serum of the animal or human is exchanged for plasma or serum which has been treated by a method as claimed in claim 32.*

*38. A method of rapidly regressing coronary atherosclerosis in an animal or a human whereby the plasma or serum of the animal or human is exchanged for plasma or serum which has been treated by a method as claimed in claim 32.*

*39. A method of removing excessive adipose tissue from an animal or a human whereby the plasma or serum of the animal is exchanged for plasma or serum which has been treated by a method as claimed in claim 32.*

*40. A method of removing fat soluble toxins from an animal or a human whereby the plasma or serum of the animal or human is exchanged for plasma or serum which has been treated by a method as claimed in claim 32.*

*41. A batch method for removing lipids from a volume of animal or human plasma, serum, or other suitable blood fraction comprising:*

*providing the volume of animal or human plasma, serum, or other suitable blood fraction;*

*admixing the plasma, serum, or other suitable blood fraction with an extraction solvent selected from hydrocarbons, ethers, alcohols, esters, amines, or mixtures thereof which extracts the lipids from the plasma, serum, or other suitable blood fraction to form a delipidated fraction;*

*introducing an absorbent to the delipidated fraction to substantially remove the solvent from the plasma, serum, or other suitable blood fraction; and*

*separating the absorbent from the delipidated fraction to form a delipidated fraction.*

*42. A method as claimed in claim 41, wherein the extraction solvent comprises a mixture of an alcohol and an ether.*

*43. A method as claimed in claim 42, wherein the extraction solvent comprises a butanol.*

*44. A method as claimed in claim 41, wherein the extraction solvent comprises butan-1-ol or butan-2-ol.*

*45. A method as claimed in claim 41, wherein the extraction solvent comprises an ether.*

*46. A method as claimed in claim 41, wherein the extraction solvent comprises di-isopropyl ether or propyl ether.*

*47. A method as claimed in claim 41, wherein the extraction solvent comprises 1-butanol and di-isopropyl ether.*

* * * * *